(12) United States Patent
Hagiya

(10) Patent No.: US 10,246,445 B2
(45) Date of Patent: Apr. 2, 2019

(54) METHOD FOR PRODUCING BENZOXAZOLE COMPOUND

(71) Applicant: Sumitomo Chemical Company, Limited, Tokyo (JP)

(72) Inventor: Koji Hagiya, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 16/076,353

(22) PCT Filed: Dec. 6, 2016

(86) PCT No.: PCT/JP2016/086174
§ 371 (c)(1),
(2) Date: Aug. 8, 2018

(87) PCT Pub. No.: WO2017/138237
PCT Pub. Date: Aug. 17, 2017

(65) Prior Publication Data
US 2019/0040049 A1 Feb. 7, 2019

(30) Foreign Application Priority Data
Feb. 12, 2016 (JP) .................................. 2016-024460

(51) Int. Cl.
*C07D 413/04* (2006.01)
*C07D 213/81* (2006.01)

(52) U.S. Cl.
CPC ......... *C07D 413/04* (2013.01); *C07D 213/81* (2013.01)

(58) Field of Classification Search
CPC .............................. C07D 413/04; C07D 213/81
See application file for complete search history.

(56) References Cited

U.S. PATENT DOCUMENTS

| | | |
|---|---|---|
| 2014/0194290 A1 | 7/2014 | Takahashi et al. |
| 2015/0189880 A1 | 7/2015 | Maehata et al. |
| 2015/0197532 A1 | 7/2015 | Takahashi et al. |
| 2015/0313234 A1* | 11/2015 | Takahashi ............ C07D 263/57 424/40 |
| 2015/0366208 A1 | 12/2015 | Shimizu et al. |
| 2016/0009715 A1 | 1/2016 | Takahashi et al. |
| 2016/0159743 A1 | 6/2016 | Takahashi et al. |
| 2017/0152270 A1 | 6/2017 | Wakamatsu et al. |

FOREIGN PATENT DOCUMENTS

| | | |
|---|---|---|
| EP | 2881386 A1 | 6/2015 |
| EP | 2952098 A1 | 12/2015 |
| EP | 3159339 A1 | 4/2017 |
| JP | 2014005263 A | 1/2014 |
| JP | 2016027019 A | 2/2016 |
| WO | 2014021468 A1 | 2/2014 |
| WO | 2014104407 A1 | 7/2014 |
| WO | 2014119679 A1 | 8/2014 |
| WO | 2015190316 A1 | 12/2015 |
| WO | 2015198817 A1 | 12/2015 |

OTHER PUBLICATIONS

Int'l Preliminary Report on Patentability dated Aug. 14, 2018 in Int'l Application No. PCT/JP2016/086174.
Int'l Search Report dated Jan. 13, 2017 in Int'l Application No. PCT/JP2016/086174.
Kolomeitsev, et al. "A Convenient Route to Aryl Trifluoromethyl Sulfones by Fluoride-Catalyzed Cross-Coupling of Arenesulfonyl Fluorides with (Trifluoromethyl)trimethylsilane and (Trifluoromethyl) trimethylstannane", Synthesis, No. 12, pp. 1151-1152, 1990.
Mouhtady, et al. "(R)-6,6?-Bis(trifluoromethanesulfonyl)-2,2?-dihydroxy-1,1?-binaphthyl: a new ligand for asymmetric synthesis", Tetrahedron Letters, vol. 47, No. 25, pp. 4125-4128, 2006.

* cited by examiner

*Primary Examiner* — Timothy R Rozof
(74) *Attorney, Agent, or Firm* — Panitch Schwarze Belisario & Nadel LLP

(57) ABSTRACT

A method is provided for producing a compound represented by formula (3), wherein n is 1, 2, 3 or 4, by mixing a compound represented by formula (2), a tri(C1-C3 alkyl)silyl(C1-C4 perfluoroalkane) and a fluoride. A method for producing the compound represented by formula (3) contains a step for producing the compound represented by formula (2) by an intramolecular dehydration condensation of a compound represented by formula (1) and by a step for mixing the compound represented by formula (2), a tri(C1-C3 alkyl)silyl(C1-C4 perfluoroalkane) and a fluoride.

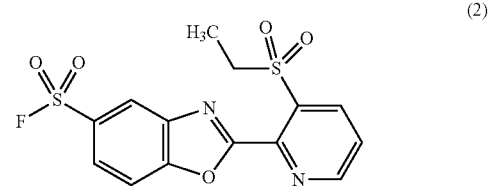

(2)

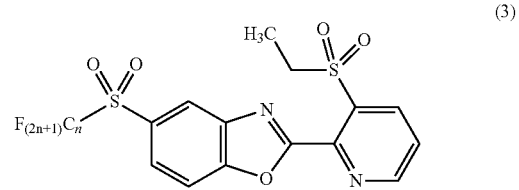

(3)

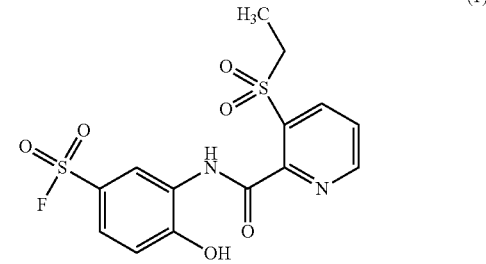

(1)

4 Claims, No Drawings

METHOD FOR PRODUCING BENZOXAZOLE COMPOUND

CROSS-REFERENCE TO RELATED APPLICATION

This application is a Section 371 of International Application No. PCT/JP2016/086174, filed Dec. 6, 2016, which was published in the Japanese language on Aug. 17, 2017, under International Publication No. WO 2017/138237 A1, which claims priority under 35 U.S.C. § 119(b) to Japanese Application No. 2016-024460, filed Feb. 12, 2016, the disclosures of which are incorporated herein by reference in their entirety.

TECHNICAL FIELD

The present invention relates to a method for preparing 2-(3-ethylsulfonylpyridin-2-yl)-5-(perfluoroalkanesulfonyl) benzoxazole having a control efficacy on harmful organisms and its preparation intermediates.

BACKGROUND ART

Patent Document 1 discloses 2-(3-ethylsulfonylpyridin-2-yl)-5-(perfluoroalkanesulfonyl)benzoxazole compound, which has a control efficacy on harmful organisms, and a process for preparing 2-(3-ethylsulfonylpyridin-2-yl)-5-(trifluoromethylsulfonyl)benzoxazole, for example, by reacting 2-amino-4-(trifluoromethylsulfanyl)phenol with 3-ethylsulfanyl picolinate followed by ring-closing and oxidizing the resulting compound.

CITATION LIST

Patent Document

Patent Document 1: WO 2014/104407 pamphlet

SUMMARY OF THE INVENTION

Problems to be Solved by Invention

The present invention provides a novel method for preparing 2-(3-ethylsulfonylpyridin-2-yl)-5-(perfluoroalkanesulfonyl)benzoxazole compound.

Means to Solve Problems

The present inventor has studied to solve the problem and, as a result, found out a method for preparing a compound represented by formula (3):

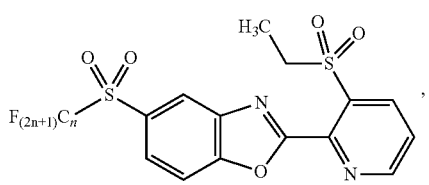

wherein n is 1, 2, 3, or 4, by mixing a compound represented by formula (2)

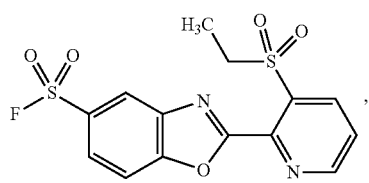

tri(C1-C3 alkyl)silyl(C1-C4 perfluoroalkane), and a fluoride.

Namely, the present invention is as follows.

[1] A method for preparing a compound represented by formula (3):

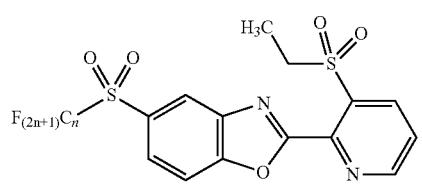

wherein n is 1, 2, 3, or 4

(hereinafter, referred to as "compound (3)"), which comprises mixing a compound represented by formula (2):

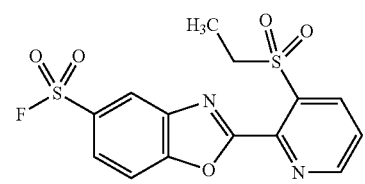

(hereinafter, referred to as "compound (2)"), tri(C1-C3 alkyl)silyl(C1-C4 perfluoroalkane), and a fluoride.

[2] A method for preparing the compound (3), which comprises a step of preparing the compound (2) by an intramolecular dehydration condensation of a compound represented by formula (1):

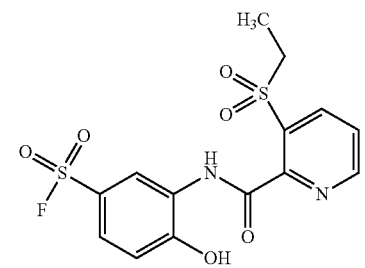

(hereinafter, referred to as "compound (1)"), and a step of mixing the compound (2), tri(C1-C3 alkyl)silyl(C1-C4 perfluoroalkane), and a fluoride.

[3] The compound (1).
[4] The compound (2).

Effect of Invention

According to the present invention, the compound (3) can be prepared by a novel process.

MODE FOR CARRYING OUT THE INVENTION

The present invention is described as follows.

Examples of the "tri(C1-C3 alkyl)silyl(C1-C4 perfluoroalkane)" include trimethylsilyl trifluoromethane, triethylsilyl trifluoromethane, triisopropylsilyl trifluoromethane, trimethylsilyl pentafluoroethane, triethylsilyl pentafluoroethane, trimethylsilyl nonafluorobutane, and trimethylsilyl heptafluoropropane, and trimethylsilyl trifluoromethane is preferred.

The "fluoride" represents alkali metal fluorides such as potassium fluoride and cesium fluoride; and quaternary ammonium fluorides such as tetrabutylammonium fluoride and 1-methyl-3-butylimidazolium fluoride, and alkali metal fluorides are preferred.

The compound (2) is prepared by an intramolecular dehydration condensation of the compound (1).

The intramolecular dehydration condensation is conducted by mixing the compound (1) with an acid, a base, phosphorus oxychloride, or a dehydration condensation agent in a solvent.

Examples of the solvent include aromatic hydrocarbons such as toluene, xylene, cumene, monochlorobenzene and tetralin; hydrocarbons such as hexane, heptane, octane, nonane and cyclohexane; ethers such as tetrahydrofuran, 2-methyltetrahydrofuran, cyclopentyl methyl ether, tert-butyl methyl ether, monoglyme and diglyme; nitriles such as acetonitrile and propylnitrile; or mixtures thereof. Among them, aromatic hydrocarbons and ethers are preferred.

A used amount of the solvent is usually within a range of 1 to 100 time(s) by weight, preferably a range of 1 to 30 time(s) by weight, relative to a weight of the compound (2).

Examples of the acid include inorganic acids such as sulfuric acid, hydrochloric acid, phosphoric acid and boric acid; and organic acids such as acetic acid, propionic acid, trifluoroacetic acid, methanesulfonic acid and p-toluenesulfonic acid.

A used amount of the acid is usually within a range of 0.1 to 5 molar ratios relative to 1 mole of the compound (1).

Examples of the base include nitrogen-containing heterocyclic compounds such as pyridine, picoline, 2,6-lutidine and 1,8-diazabicyclo[5.4.0]-7-undecene; tertiary amines such as triethylamine and N,N-diisopropylethylamine; and inorganic bases such as sodium hydride and potassium carbonate.

A used amount of the base is usually within a range of 1 to 5 molar ratio(s) relative to 1 mole of the compound (1).

A used amount of phosphorus oxychloride is usually within a range of 1 to 5 molar ratio(s) relative to 1 mole of the compound (1).

Examples of the dehydration condensation agent include acetic anhydride, trifluoroacetic anhydride, and diethyl azodicarboxylate, and its used amount is usually within a range of 1 to 5 molar ratio(s) relative to 1 mole of the compound (1).

The reaction is conducted by heating within the temperature of usually a range of 50° C. to 200° C., preferably a range of 100° C. to 200° C. A reaction period of the reaction is within a range of 0.1 to 24 hours.

After the reaction is completed, for example, water is added thereto, and the mixture is neutralized with an acidic solution or an alkaline solution, and the mixture may be extracted with an organic solvent, and the organic solvent may be then removed by distillation to give the compound (2). The compound (2) can be further purified by crystallization and column chromatography and the like.

The compound (1) is prepared by reacting 3-amino-4-hydroxybenzenesulfonyl fluoride with 3-ethylsulfonyl-2-pyridine carbonyl chloride in an aprotic solvent.

Examples of the aprotic solvent include aromatic hydrocarbons such as toluene, xylene, cumene, monochlorobenzene and tetralin; hydrocarbons such as hexane, heptane, octane, nonane and cyclohexane; ethers such as tetrahydrofuran, 2-methyltetrahydrofuran, cyclopentyl methyl ether, tert-butyl methyl ether, monoglyme and diglyme; nitriles such as acetonitrile and propylnitrile; or mixtures thereof.

A used amount of the aprotic solvent is usually within a range of 1 to 20 time(s) by weight relative to a weight of 3-amino-4-hydroxybenzenesulfonyl fluoride.

3-Amino-4-hydroxybenzenesulfonyl fluoride is a commercially available compound, or can be prepared, for example, according to the method described in J. Agr. Food Chem., Vol. 17, 810-817.

3-Ethylsulfonyl-2-pyridine carbonyl chloride can be prepared, for example, according to the method described in WO 2014/104407.

In addition, the compound (1) is prepared also by reacting a compound represented by the following formula (1X):

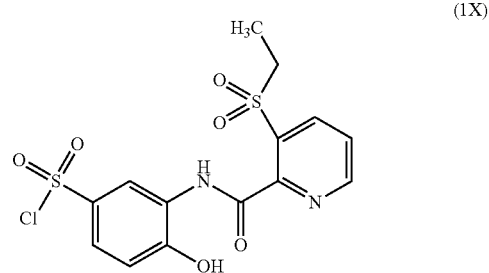 [SMILES: CCS(=O)(=O)c1cccnc1C(=O)Nc1cc(S(=O)(=O)Cl)ccc1O]

(1X)

(hereinafter, referred to as "compound (1X)") with a fluoride in an aprotic polar solvent.

Examples of the fluoride include alkali metal fluorides such as potassium fluoride and cesium fluoride; and quaternary ammonium fluorides such as tetrabutylammonium fluoride and 1-methyl-3-butylimidazolium fluoride; and the like.

A used amount of the fluorinating agent is usually within a range of 1 to 3 molar ratio(s) relative to 1 mole of the compound (1X).

Examples of the aprotic polar solvent include ethers such as tetrahydrofuran, diethyl ether and dibutyl ether; nitriles such as acetonitrile and propionitrile; amides such as N,N-dimethylformamide, N,N-dimethylacetamide and N-methylpyrrolidone; and sulfur-containing compounds such as ethyl methyl sulfone and sulfolane.

A used amount of the aprotic polar solvent is usually within a range of 1 to 20 time(s) by weight relative to a weight of the compound (1X).

The compound (1X) can be prepared, for example, according to the method described in Phosphorus and Sulfur and the Related Elements, Vol. 12, 197-204.

Next, a process for preparing the compound (3) by mixing the compound (2), tri(C1-C3 alkyl)silyl(C1-C4 perfluoroalkane), and a fluoride is described.

The reaction is usually conducted in the presence of a solvent.

Examples of the solvent include aromatic hydrocarbons such as toluene, xylene, cumene, monochlorobenzene and tetralin; hydrocarbons such as hexane, heptane, octane, nonane and cyclohexane; sulfur-containing compounds such as dimethyl sulfoxide and sulfolane; ethers such as tetrahydrofuran, 2-methyltetrahydrofuran, cyclopentyl methyl ether, tert-butyl methyl ether, monoglyme and diglyme; amides such as N,N-dimethylacetamide, N,N-dimethylformamide and N-methylpyrrolidone; nitriles such as acetonitrile and propylnitrile; or mixtures thereof. Among them, ethers and amides are preferred.

A used amount of the solvent is usually within a range of 1 to 100 time(s) by weight, preferably within a range of 1 to 30 time(s) by weight, relative to a weight of the compound (1).

An amount of the tri(C1-C3 alkyl)silyl(C1-C4 perfluoroalkane) used in the reaction is usually within a range of 1 to 10 molar ratio(s) relative to 1 mole of the compound (1), and an amount of the fluoride used in the reaction is usually within a range of 0.1 to 2 molar ratios relative to 1 mole of the compound (1).

A reaction temperature of the reaction is usually within a range of −20° C. to 200° C., preferably within a range of 0° C. to 160° C.

A reaction period of the reaction is within a range of a few minutes to 48 hours.

After the reaction is completed, for example, water is added thereto, and the mixture may be extracted with an organic solvent, and the organic solvent may be then removed by distillation to give the compound (3). The obtained compound (3) may be purified by crystallization and column chromatography.

Examples of the compound (3) include 2-(3-ethylsulfonylpyridin-2-yl)-5-(trifluoromethylsulfonyl)benzoxazole, and 2-(3-ethylsulfonylpyridin-2-yl)-5-(pentafluoroethylsulfonyl)benzoxazole.

EXAMPLE

Hereinafter, the present invention is specifically explained by the examples, however, the present invention should not be limited to the examples.

Measurement condition for high performance liquid chromatography
Apparatus: Manufactured by SHIMADZU CORPORATION
Mobile phase: A solution: 0.1% phosphoric acid solution, B solution: acetonitrile
Column: SUMIPAX (registered trademark) ODS Z-CLUE (manufactured by Sumika Chemical Analysis Service, Ltd.), inner diameter 4.6 mm, length 100 mm, particle diameter 3 μm
Column temperature: 40° C.
Flow rate: 1.0 mL/min
UV wavelength: 250 nm
Injection volume: 10 μl
Internal standard substance: acetanilide

| Time program: | |
|---|---|
| Time (min) | B conc (%) |
| 0 | 10 |
| 40 | 90 |
| 50 | 90 |
| 50.1 | 10 |
| 60 | 10 |

Measurement condition for gas chromatography mass spectrometer
Apparatus: Manufactured by Agilent MSD HP5973
Column: DB-1, length 30 m, inner diameter 250 μm, film thickness 0.25 μm
Column temperature: heating from 50° C. to 300° C. at the rate of 10° C./min, followed by holding at 300° C. for 5 minutes
Flow rate of helium gas: 1.0 mL/min
Injection volume: 1 μl Example 1

3-Ethylsulfonyl-N-[2-hydroxy-5-(fluorosulfonyl)phenyl]picolinamide 50 mg, para-toluenesulfonic acid monohydrate 40 mg, and chlorobenzene 5 g were mixed and stirred at 150° C. under a nitrogen atmosphere for 5 hours. After the reaction was completed, the reaction mixture was cooled to room temperature, thereto was added water 3 g, and the mixture was stirred and separated with a separatory funnel. The resulting organic layer was dried over magnesium sulfate and filtrated. The filtrate was concentrated to dryness to give 2-(3-ethylsulfonylpyridin-2-yl)-5-(fluorosulfonyl)benzoxazole as a pale yellow solid with a yield of 50 mg (purity 90%).
$^1$H-NMR (CDCl$_3$) δ: 8.99 (1H, d), 8.52 (1H, dd), 8.50 (1H, dd), 8.18 (1H, dd), 7.41 (1H, d), 7.29 (1H, dd), 3.92 (2H, q), 1.38 (3H, t)

Example 2

3-Ethylsulfonyl-N-[2-hydroxy-5-(fluorosulfonyl)phenyl]picolinamide 2.0 g, para-toluenesulfonic acid monohydrate 1.0 g, and xylene 10 g were mixed, and the mixture was heated to 160° C. under a nitrogen atmosphere, and then stirred at reflux for 5 hours. After the reaction was completed, the reaction mixture was cooled to room temperature, thereto was added water 10 g, and the mixture was stirred and separated with a separatory funnel. The resulting organic layer was dried over magnesium sulfate and filtrated. The filtrate was concentrated to dryness to give 2-(3-ethylsulfonylpyridin-2-yl)-5-(fluorosulfonyl)benzoxazole.

Example 3

Under a nitrogen atmosphere, 2-(3-ethylsulfonylpyridin-2-yl)-5-(fluorosulfonyl)benzoxazole 100 mg, potassium fluoride 20 mg, trimethylsilyl trifluoromethane 120 mg, and tetrahydrofuran 2 g were added to a glass pressurized vessel, and the mixture was stirred at 100° C. for 5 hours.

When the reaction mixture was analyzed using a high-performance liquid chromatography with an internal reference method, it was confirmed that the yield of 2-(3-ethylsulfonylpyridin-2-yl)-5-(trifluoromethylsulfonyl)benzoxazole was 60%.

Example 4

Under a nitrogen atmosphere, 2-(3-ethylsulfonylpyridin-2-yl)-5-(fluorosulfonyl)benzoxazole 50 mg, potassium fluoride 10 mg, trimethylsilyl trifluoromethane 60 mg, and tetrahydrofuran 1 g were added to a flask, and the mixtures was stirred at 50° C. for 30 minutes.

When the reaction mixture was analyzed using a high-performance liquid chromatography with an internal reference method, it was confirmed that the yield of 2-(3-ethylsulfonylpyridin-2-yl)-5-(trifluoromethylsulfonyl)benzoxazole was 39%.

Example 5

Under a nitrogen atmosphere, 2-(3-ethylsulfonylpyridin-2-yl)-5-(fluorosulfonyl)benzoxazole 50 mg, cesium fluoride 3 mg, trimethylsilyl trifluoromethane 39 mg, and tetrahydrofuran 1 g were added to a flask, and the mixture was stirred at 25° C. for 2 hours.

When the reaction mixture was analyzed using a high-performance liquid chromatography with an internal reference method, it was confirmed that the yield of 2-(3-ethylsulfonylpyridin-2-yl)-5-(trifluoromethylsulfonyl)benzoxazole was 79%.

Comparative Example 1

Under a nitrogen atmosphere, 2-(3-ethylsulfonylpyridin-2-yl)-5-(fluorosulfonyl)benzoxazole 50 mg, tris(dimethylamino)sulfonium difluorotrimethylsilane 4 mg, trimethylsilyl trifluoromethane 40 mg, and tetrahydrofuran 1 g were added to a flask, and the mixture was stirred at 25° C. for 2 hours.

When the reaction mixture was analyzed using a high-performance liquid chromatography with an internal reference method, it was confirmed that the yield of 2-(3-ethylsulfonylpyridin-2-yl)-5-(trifluoromethylsulfonyl)benzoxazole was 5%.

Reference Preparation Example 1

Under a nitrogen atmosphere, 3-amino-4-hydroxybenzenesulfonyl fluoride 500 mg, 3-ethylsulfonyl-2-pyridine carbonyl chloride 615 mg, and tetrahydrofuran 5 g were added to a flask, and the mixture was stirred at 60° C. for 2 hours. After the reaction mixture was cooled to room temperature, to the reaction solution were added water 10 g and ethyl acetate 10 g, and the reaction mixture was stirred and separated with a separatory funnel. The resulting organic layer was washed with water 10 g and then dried over magnesium sulfate and filtrated. The organic layer was concentrated to give the crude product, and the crude product was purified using a silica gel column chromatography to give 3-ethylsulfonyl-N-[2-hydroxy-5-(fluorosulfonyl)phenyl]picolinamide.

$^1$H-NMR (CDCl$_3$) δ: 10.00 (1H, s), 8.82 (1H, s), 8.71 (1H, d), 7.99 (1H, d), 7.55 (1H, dd), 7.49 (1H, d), 6.99 (1H, d), 3.90 (2H, q), 1.20 (3H, t)

Reference Preparation Example 2

Under a nitrogen atmosphere, 3-amino-4-hydroxybenzenesulfonyl fluoride 1.2 g, a xylene solution containing 3-ethylsulfonyl-2-pyridine carbonyl chloride in 50% 3.0 g, and tetrahydrofuran 5 g were added to a flask, and the mixture was stirred at 60° C. for 2 hours. After the reaction mixture was cooled to room temperature, to the reaction solution were added water 10 g and ethyl acetate 30 g, and the reaction mixture was stirred and separated with a separatory funnel. The resulting organic layer was washed with water 10 g and then dried over magnesium sulfate and filtrated. The organic layer was concentrated to give 2.0 g of 3-ethylsulfonyl-N-[2-hydroxy-5-(fluorosulfonyl)phenyl]picolinamide as a crude product.

INDUSTRIAL APPLICABILITY

According to the present invention, 2-(3-ethylsulfonylpyridin-2-yl)-5-(perfluoroalkanesulfonyl)benzoxazole compound can be prepared.

The invention claimed is:

1. A method for preparing a compound represented by formula (3):

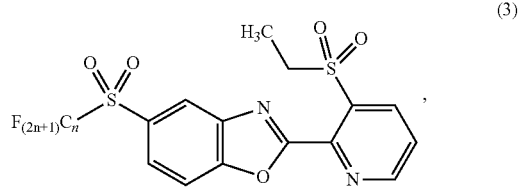

wherein n is 1, 2, 3, or 4, which comprises mixing a compound represented by formula (2)

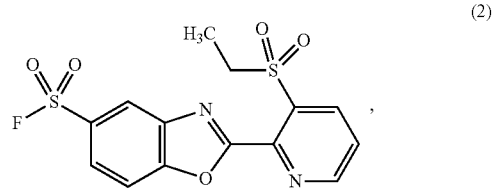 [SMILES: CCS(=O)(=O)c1cccnc1-c1nc2cc(S(=O)(=O)F)ccc2o1]

tri(C1-C3 alkyl)silyl(C1-C4 perfluoroalkane), and a fluoride.

2. A method for preparing a compound represented by formula (3):

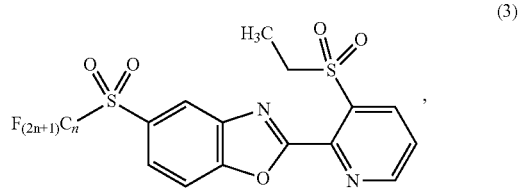

wherein n is 1, 2, 3, or 4, which comprises a step of preparing a compound represented by formula (2):

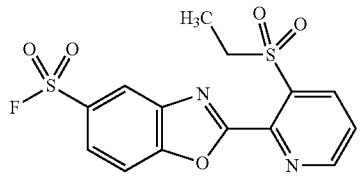
by an intramolecular dehydration condensation of a compound represented by formula (1):
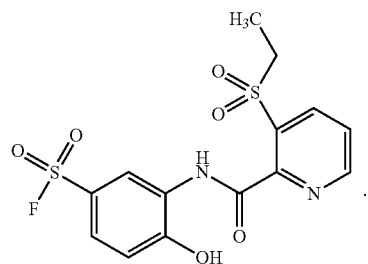
and a step of mixing the compound represented by formula (2), tri(C1-C3 alkyl)silyl(C1-C4 perfluoroalkane), and a fluoride.
3. A compound represented by formula (1):
4. A compound represented by formula (2):
* * * * *